United States Patent [19]

Parker et al.

[11] 4,318,296

[45] Mar. 9, 1982

[54] SAMPLING EQUIPMENT FOR SEDIMENTATION RATE MEASURING

[75] Inventors: David S. Parker; Stephen R. Shaw; Robert Hudson, all of Burton-on-Trent, England

[73] Assignee: Coal Industry (Patents) Limited, London, England

[21] Appl. No.: 144,113

[22] Filed: Apr. 28, 1980

[30] Foreign Application Priority Data

May 23, 1979 [GB] United Kingdom ............... 18035/79

[51] Int. Cl.³ ............................................. G01N 15/04
[52] U.S. Cl. .................................................... 73/61.4
[58] Field of Search ......................... 73/61.4; 356/335; 250/577

[56] References Cited

U.S. PATENT DOCUMENTS

| | | | |
|---|---|---|---|
| 3,254,527 | 6/1966 | Noller | 74/61.4 |
| 3,812,966 | 5/1974 | Beach et al. | 73/61.4 X |
| 4,194,391 | 3/1980 | Rosenberg | 73/61.4 |

*Primary Examiner*—S. Clement Swisher
*Attorney, Agent, or Firm*—James C. Wray

[57] ABSTRACT

Sampling equipment is provided for sensing and controlling the settling rate of a flocculated slurry suspension in a settling tank, the sampling equipment comprises a metering device (23) including a vertical settling chamber for repeatedly taking a sample of the suspension from the settling tank. Means (33, 35, 19) are provided for temporarily retaining the height of the sample at a preselected level during a settling period and detector means (40, 41, 42) are provided for detecting when a boundary level defined by the settling solids reaches a further preselected level. Timer means determine the actual settling period elapsing between the start of the settling period and the time when the boundary level has reached the further preselected level.

13 Claims, 7 Drawing Figures

SAMPLING EQUIPMENT FOR SEDIMENTATION RATE MEASURING

This invention relates to sampling equipment for sensing the settling periods of suspensions.

In particular, although not exclusively, the present invention relates to sampling equipment for sensing and controlling the settling rate of flocculated slurry in settling tanks of coal preparation plants. The sampling equipment senses the actual settling period of a sample of the slurry and compares the actual settling period against a desired settling period, any difference between the actual settling period and the desired settling period being used to control the rate of addition of flocculant to the settling tank.

It is known for such sampling equipment to comprise a metering device for taking a sample having a preselected volume from the settling tank, the sample being fed from the metering device to a settling chamber where the settling period of the suspension is sensed by a pair of vertically spaced photo-electric cell devices arranged to detect when a boundary defined by the settling solids reaches the associated preselected level. It will be appreciated that as the solid particles in the suspension settle a boundary level is defined between the settling solids and the relatively clear liquid. The period of time between the two photo-electric cell devices indicating that the boundary level defined by the settling solids has reached the associated levels is used in an attempt to determine the settling period of the sample which is indicative of the settling rate of the slurry in the settling tank.

Unfortunately, the boundary level defined by the settling solids tends not to have stabilised by the time the first preselected level is reached and the associated photo-electric cell device tends to give unreliable results. Hence, such prior known sampling equipment tends to be unsatisfactory for controlling the rate of addition of flocculant to the settling tank.

An object of the present invention is to provide sampling equipment which tends to give more reliable results than the previously known sampling equipment and which is compact and relatively simple.

According to the present invention, sampling equipment for use in sensing the settling rate of a suspension comprises a metering device for taking a sample of the suspension, the metering device comprising a sampling chamber for the sample, timer means for controlling control means to stop the feed of suspension to the sampling chamber, means for retaining the height of the sample at a preselected level in the sampling chamber during a settling period, and detector means for detecting when a boundary level defined by the settling solids in the sample in the sampling chamber reaches a further preselected level, the timer means determining the period of time elapsing between the start of the settling period when the height of the sample is at the preselected level and the time when the detector means detects the boundary level has reached the further preselected level.

Preferably, the timer means compares the actual settling period elapsing between the start of the settling period and the time when the detector means detects the boundary level has reached the further preselected level against a preselected optimum desired settling period.

Advantageously, the timer means compares the actual settling periods.

Conveniently, the timer means comprises controller/timer means for controlling the control means for a period of time dependent upon the difference between the actual settling period and the or at least one of the preselected desired settling periods.

Preferably, the control means also controls the setting of a flow control valve controlling the rate of feed of flocculant into the suspension.

Conveniently, the detector means comprises a photo-electric cell device.

Advantageously, the photo-electric cell device comprises a light source arranged on one side of the settling chamber and a light sensitive receiver arranged on the opposite side of the settling chamber to the light source.

Preferably, the sampling equipment comprises compressor means having two alternative operational modes in which it applies suction and pressure to the settling chamber, respectively, operation of the compressor means being controlled by the timer means.

Conveniently, the means for retaining the height of the sample at a preselected level during the settling period comprises a pipe extending into the settling chamber, the end of the pipe defining the preselected level.

Advantageously, excess suspension is urged to flow along the pipe when the settling chamber is pressurised by the compressor means.

Alternatively, the means for retaining the height of the sample of the preselected level during the settling period comprises a weir.

Preferably, further detector means are provided to sense when the height of the sample in the settling chamber has reached or passed the preselected level.

Preferably, the further detector means comprises a capacitance detector having probes extending into the settling chamber.

Alternatively, the further detector means comprises a photoelectric cell device.

Preferably, discharge valve means are provided at the base of the settling chamber, the discharge valve means being actuated by the timer means to discharge the sample from the settling chamber at the end of the settling period.

By way of example only, two embodiments of the present invention will be described with reference to the accompanying drawings, in which.

Figure 1:
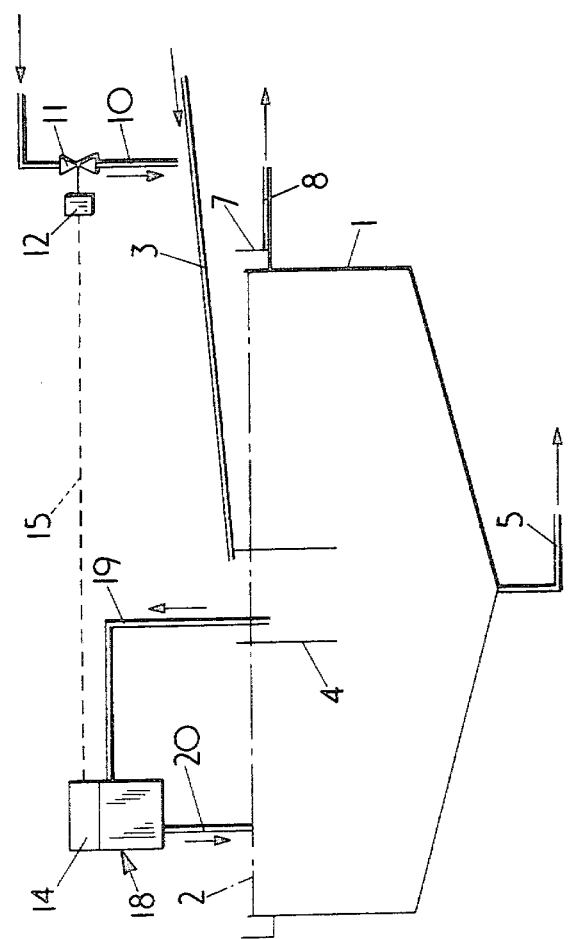
FIG. 1 is a diagrammatic layout of a part of a coal preparation plant including a settling tank for flocculated slurry and sampling equipment for sensing the settling rate of the slurry and for controlling the rate of feed of flocculant into the settling tank.
Figure 4:
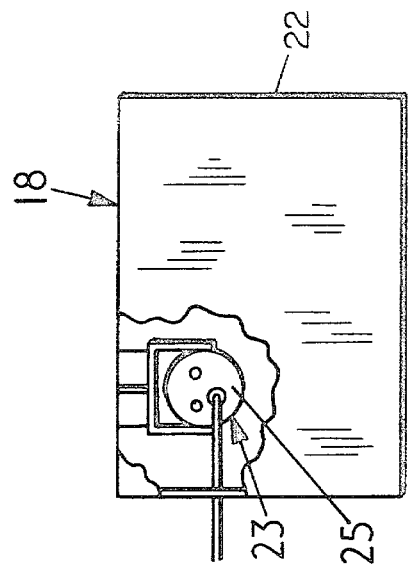
FIG. 4 is an incomplete, partly cut away plan of the equipment of FIG. 2.
Figure 3:
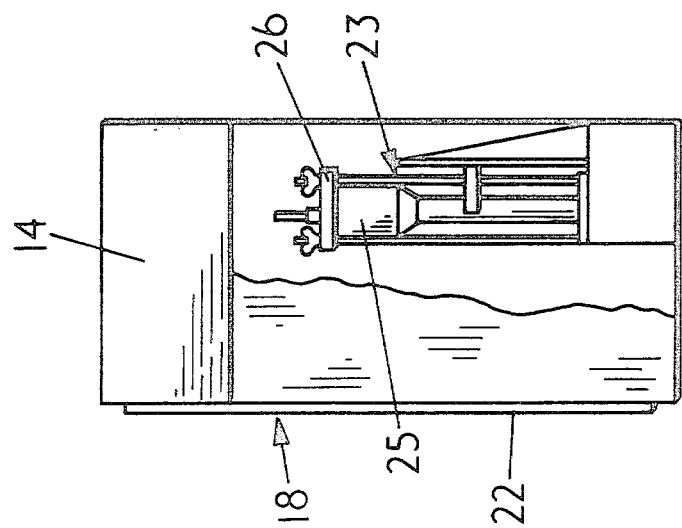
FIG. 3 is an incomplete, partly cut away side view of the equipment of FIG. 2.

FIG. 1 of the drawings shows a part of a coal preparation plant comprising a settling tank or thickener 1 only the outline of which is shown and which is filled up to level 2 with flocculated slurry. Slurry to be treated is fed continuously along a launder 3 into a central zone of the settling tank shielded from the remainder of the settling tank by an open ended cylindrical guide 4. Settled solids are removed by the bottom of the settling tank at a desired controlled rate via a discharge pipe 5 while relatively clear or clarified water is allowed to over flow the outer periphery of the settling tank wall into a collection trough 7 and subsequently to a discharge pipe 8.

Flocculant required to accelerate the settling rate of the slurry in the settling tank is added to the slurry as it is conveyed along the launder 3, the flocculant being fed at a controlled rate via feed pipe 10 and an electrically operated flow control valve 11 having control means 12 for controlling the setting of the control valve in response to a control signal fed from controller/timer means 14 along line 15, the operation of the timer means which together with the control valve constitute part of sampling equipment for sensing the settling rate of the slurry in the settling tank and for controlling rate of feed of flocculant into the tank, will be described in more detail later in the specification.

The timer means 14 constitutes part of a metering and sampling control unit 18 arranged to repeatedly draw samples of the slurry suspension from the central zone of the settling tank via pipe 19 and to return the samples back into the settling tank after processing via discharge pipe 20. Typically, the metering and sampling device repeatedly draws a fresh sample along pipe 19, processes the sample and return the processed sample to tank every two minutes.

FIGS. 2, 3, 4 and 5 show the metering and sampling control unit 18 to comprise a cabinet 22 within which is mounted a metering device 23 (see particularly FIG. 5) comprising a closed vertical settling chamber 25 having a relatively large diameter upper portion containing detector means for detecting when the height of the suspension sample in the settling chamber reaches a preselected desired maximum level and a relatively small diameter light transparent lower portion. The top of the relatively large diameter portion of the settling chamber 25 is closed by a cap 26 permitting the sealed entry of two probes 28 and 29 into the settling chamber. The probes 28 and 29 constitute part of a conductance detector arranged to detect when the height of the sample in the settling chamber reaches a desired maximum level determined by the position of the lowermost extents of sensitive parts of the probes. In operation the conductance across the two probes changes when the upper level of the sample contacts the sensitive parts of the probes, this change in the conductance is sensed by the conductance detector 30 which thereby derives a signal indicative that the height of the upper level of the sample has reached the desired maximum level, the indicative derived signal is then fed to a sampler/timer control panel 60 which actuates compressor means 32 arranged to draw suspension from the central zone of the settling tank via pipe 19. The compressor means 32 has two alternative operation modes in which it applies suction and pressure to the settling chamber 25, respectively, the suction or pressure being affected via pipe 33 connected to the settling chamber 25 via the cap 26. A float-valve 34 is provided at the mouth of the pipe 33 to ensure no suspension can be drawn into the compressor means 32 should the action of the conductance detector fail to cut off the compressor means sufficiently quickly.

Figure 5:
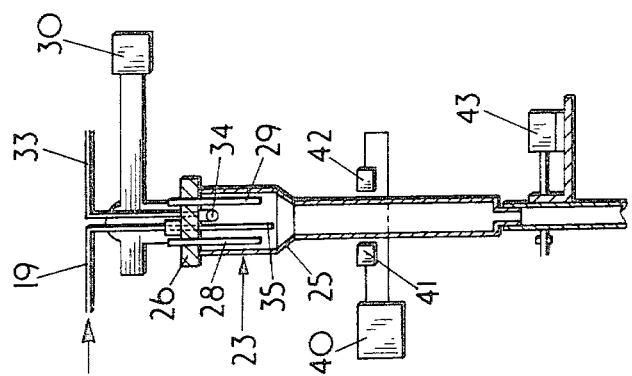
FIG. 5 is an incomplete sectional front view of a detail of FIG. 2 drawn on an enlarged scale.

When the compressor means 32 applies suction to the settling chamber 25 suspension is drawn along pipe 19 and into the settling chamber, from FIG. 5 it can be seen that the end 35 of the pipe 19 extends through the cap 26 down into the relatively large diameter portion of the settling chamber 25 below the probes 28 and 29. Thus, the sample of suspension is drawn into the settling chamber 25 via pipe 19 until the probes 28 and 29 detect that the desired maximum level has been reached. By this time the end 35 of the pipe 19 is submerged beneath the upper level of the sample. As mentioned previously, the conductance detector 30 then derives an indicative signal which is fed via the timer means 60 to actuate the compressor means 32 from its suction mode into its pressure mode in which the settling chamber 25 is pressurised for a preselected period of time. During the time the settling chamber is pressurised flocculant is urged to flow along pipe 19 from the settling chamber 25 back into the settling tank 1. This return of suspension continues until the height of the upper level of the sample in the settling chamber reaches the lowermost end 35 of the pipe 19 when the air pressure is short circuited into pipe 19. Thus, the height of the upper level of the sample in the settling chamber is temporarily retained constant at a preselected level determined by the lowermost extent of the end 35 of the pipe 19.

After a preselected period of time the sampler/timer means 60 deactuates the compressor means allowing the solids suspended in the sample in the settling chamber to start to settle. The time when the settling period begins, that is, when the compressor means is deactuated, is monitored by the controller/timer means 14. The preselected period of time for which the compressor means pressurised the settling chamber is just sufficient for the upper level of the sample to reach the lowermost end 35 of the pipe 19, the minimum period of time required being determined by experience and practical tests.

The solids suspended in the sample in the settling chamber 25 are allowed to settle until the upper boundary defined by the settling solids leaving an upper relatively clear liquid zone reaches a preselected level determined by the location of photo-electric cell device 40 having a light emitter 41 arranged on one side of the relatively small diameter transparent portion of the settling chamber and a light sensitive receiver 42 arranged on the opposite side of the transparent portion of the settling chamber. Thus in operation, as soon as the upper boundary level defined by the settling solids reaches the preselected level determined by the photo-electric cell device 40, 41 and 42, the relatively clear liquid zone permits light rays from the emitter 41 to reach the receiver 42 and the photo-electric cell device derives a signal indicative that the relative clear liquid zone has reached the preselected level, the derived signal being fed to the controller/timer means 14.

Upon the controller/timer means 14 receiving the signal from the photo-electric cell device it determines the period of time elapsing between the start of the settling period and the time the photo-electric cell device derived signal is received and thereby determines the actual settling period required by the solids in the suspension to settle from the first preselected level determined by the lowermost end 35 of the pipe 19 to the second preselected level determined by the location of the photo-electric cell device 40, 41 and 42.

The controller/timer means 14 compares the actual settling period with an optimum desired settling period and with preselected minimum and maximum desired settling periods and suitably actuates the control means 12 of the flocculant flow control valve 11 which in normal operation is about midway between its fully open and fully closed positions. Typically the optimum desired settling periods is one minute and the minimum and maximum desired settling periods are one half minute and one and one half minutes, respectively.

If the photo-electric cell device derives its indicative signal before the minimum desired settling period is reaches ie the solids are settling far too rapidly when the controller/timer device 14 causes the control means 12 to tend to close the flocculant flow control valve 11 for a period of time equal to the difference between the minimum desired settling period and the optimum desired settling period. In the above typical example the flocculant flow control valve would be urged to close for one half minute.

If the photo-electric cell device derives its indicative signal after the minimum desired settling period but before the optimum desired settling period is reached then the controller/timer device 14 causes the control means 12 to tend to close the flocculant flow control valve 11 for a period of time equal to the difference between the optimum desired period and the actual settling period. Thus, in the above typical example, if the actual settling period is three-quarters of a minute, then the flocculant flow control valve would be urged to close for one quarter of a minute.

If the photo-electric cell device derived its indicative signal after a settling period equal with the optimum desired period then no adjustment of the flocculant flow control valve is required.

If the photo-electric cell device derived its indicative signal at a time after the optimum desired period but before the maximum desired period (ie the solids are settling too slowly), then the controller/timer means 14 would cause the control means 12 to open further the flocculant flow control valve 11 for a period equal to the difference between the actual settling period and the optimum desired settling period. Thus, in the above typical example, if the actual settling period is one and one quarter minutes the flocculant flow control valve 11 would be urged to open further for one quarter of a minute.

If the photo-electric cell device derived its indicative signal at a time after the maximum desired settling period, the flocculant flow control valve 11 would be opened further for a period of time equal to the difference between the maximum desired settling period and the optimum desired settling period. Thus, in the above typical example, the flocculant flow control valve 11 would be urged to open further for one half minute.

After the controller/timer device 14 has received the signal derived by the photo-electric cell device and suitably adjusted the setting of the flocculant flow control valve as explained above, the sample is discharged from the settling chamber 25 back into the settling tank via the discharge pipe 20. During the discharge the sampler/timer means 60 actuates a solenoid operated valve 43 to open the pipe 20 and actuates the compressor means 32 to feed pressure to the settling chamber to urge the sample out of the settling chamber.

After a preselected period of time, which from experience is just sufficient for the sample to be discharged from the sample the timer means causes the valve 43 to close pipe 20, the pressurised air from the compressor means 32 being maintained for a period after the closure of the valve 43 in order to clear out any suspension from the feed pipe 19. The sampler/timer means 60 than reactivates the whole cycle by first causing the compressor means to apply suction to the settling chamber 25 to draw a fresh sample of suspension into the settling chamber. The whole of the above described precedure then is repeated for the fresh sample. As previously stated in a typical example the whole cycle is repeated approximately every two minutes so that an effectively continuous sampling and control procedure is maintained.

Figure 2:
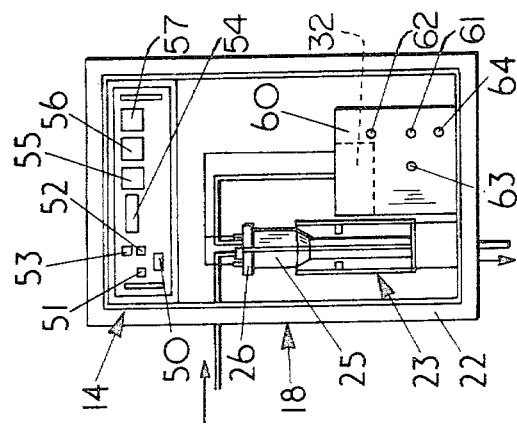
FIG. 2 is a front view of the sampling equipment of FIG. 1, the sampling equipment being constructed in accordance with the present invention and being drawn on an enlarged scale to FIG. 1.

FIG. 2 shows that the controller/timer means 14 is mounted in the cabinet 22 with its front panel comprising various indicators and instruments including an on-off switch indicator 50, flocculant flow control valve opening and closing mode indicators 51 and 52, respectively, and a settling period complete indicator 53. Also an actual settling period indicator 54 is provided together with settling dials 55, 56 or 57 showing the preselected minimum desired settling period, the preselected optimum desired settling period and the preselected maximum desired settling period, respectively.

The sampler/timer control panel 60 for the metering device including the settling chamber 25 includes the compressor means 32, an on/off switch and an on/off indicator 62. The sampler/timer control panel 60 also includes a manual override switch 63 and a fuse compartment 64.

In a modified arrangement of the first described embodiment of the present invention the conductance detector 30 is replaced by a photo-electric cell device including a hysterisis characteristic which permits some over run by the upper level of the sample tending to ensure the adjacent portions of the transparent settling chamber are kept clean.

Figure 7:
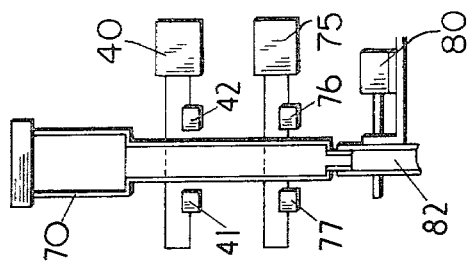
FIG. 7 is an incomplete front view of the detail of FIG. 6, the detail being viewed in a direction normal to that of FIG. 6.
Figure 6:
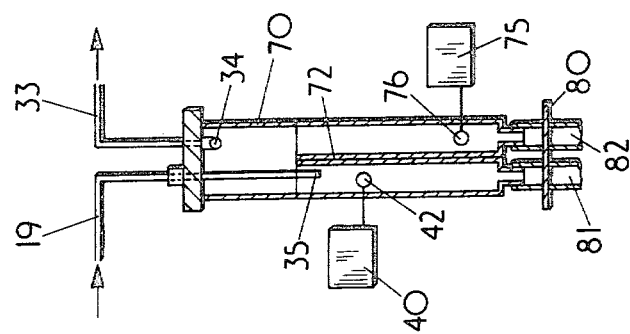
FIG. 6 is an incomplete sectional side view similar to FIG. 5 but showing a detail of a second embodiment of the present invention.

FIGS. 6 and 7 show a detail of a second embodiment of the present invention in which the cylindrical settling chamber 25 of the first described embodiment has been replaced by a settling chamber 70 including an internal weir 72 which determines the preselected level at which the upper level of the sample in the settling chamber is temporarily retained during the settling period. In use, the timer means causes the compressor means to apply suction to the settling chamber 70 via pipe 33 so that suspension is drawn from the settling tank along pipe 19 into the settling chamber on one side of the weir 72, the end 35 of the pipe 19 extending to below the upper limit of the weir. The compressor means is actuated to draw suspension from the settling tank until it overflows the weir and starts to collect in the portion of the settling chamber on the opposite side of the weir. The excess suspension continues to overflow the weir until the level on the opposite side of the weir reaches a preselected level determined by a photo-electric cell device 75 including a light emitter 76 and a light sensitive receiver 77 mounted on opposite sides of the settling chamber 72 as seen in FIG. 7.

Upon the overflow suspension level reaching this preselected level determined by the photo-electric cell device 75, the device 75 derives an indicative signal which is fed to the timer means which thereby causes the compressor means to be deactuated and which also times the actual settling period for the upper boundary level defined by the settling solids to reach the preselected level determined by the photo-electric cell device 40, 41 and 42 in similar manner to that previously explained with reference to the first described embodiment.

As with the first described embodiment the actual settling period is compared with the optimum desired settling period and with the maximum and minimum desired settling periods and the flocculant flow control valve suitably controlled.

Upon completion of the settling period, the timer means causes a dual solenoid valve 80 to open permitting the discharge of the sample along discharge pipes 81 and 82 from the settling chamber 70 back to the settling tank.

The whole sampling and controlling process is repeated in similar manner to the first described embodiment. However, with the second embodiment the height of the sample is temporarily retained at the preselected level during the settling period by the weir 72 and not by the siting of the lowermost end 35 of the pipe 19.

From the above description it will be seen that the present invention provides sampling equipment for use in controlling the settling rate of flocculated suspensions, the equipment being reliable, compact and relatively simple.

We claim:

1. Sampling equipment for use in sensing the settling rate of a suspension, comprising a metering device for taking a sample of the suspension, the metering device comprising a sampling chamber for the sample, timer means for controlling control means to stop the feed of suspension to the sampling chamber, means for retaining the height of the sample at a preselected level in the sampling chamber during a settling period, and detector means for detecting when a boundary level defined by the settling solids in the sample reaches a further preselected level, the timer means determining the period of time elapsing between the start of the settling period when the height of the sample is at the preselected level and the time when the detector means detects the boundary level has reached the further preselected level, in which the timer means compares the actual settling period elapsing between the start of the settling period and the time when the detector means detects the boundary level has reached the further preselected level against a preselected optimum desired settling period.

2. Equipment as claimed in claim 1, in which the timer means compares the actual settling period against preselected minimum and/or maximum desired settling periods.

3. Equipment as claimed in claim 1, in which the timer means comprises controller/timer means for controlling control means for a period of time dependent upon the difference between the actual settling period and the or at least one of the preselected desired settling periods.

4. Equipment as claimed in claim 3, in which the control means controls the setting of a flow control valve controlling the rate of feed of flocculant into the suspension.

5. Equipment as claimed in claim 1, in which the detector means comprises a photo-electric cell device.

6. Equipment as claimed in claim 1, comprising compressor means having two alternative operational modes in which it applies suction and pressure to the settling chamber, respectively, operation of the compressor means being controlled by the timer means.

7. Sampling equipment for use in sensing the settling rate of a suspension, comprising a metering device for taking a sample of the suspension, the metering device comprising a sampling chamber for the sample, timer means for controlling control means to stop the feed of suspension to the sampling chamber, means for retaining the height of the sample at a preselected level in the sampling chamber during a settling period, and detector means for detecting when a boundary level defined by the settling solids in the sample reaches a further preselected level, the timer means determining the period of time elapsing between the start of the settling period when the height of the sample is at the preselected level and the time when the detector means detects the boundary level has reached the further preselected level, in which the means for temporarily retaining the height of the sample at a preselected level during the settling period comprises a pipe extending into the settling chamber, the end of the pipe defining the preselected level.

8. Equipment as claimed in claim 7, in which excess suspension is urged to flow along the pipe when the settling chamber is pressurised by the compressor means.

9. Sampling equipment for use in sensing the settling rate of a suspension, comprising a metering device for taking a sample of the suspension, the metering device comprising a sampling chamber for the sample, timer means for controlling control means to stop the feed of suspension to the sampling chamber, means for retaining the height of the sample at a preselected level in the sampling chamber during a settling period, and detector means for detecting when a boundary level defined by the settling solids in the sample reaches a further preselected level, the timer means determining the period of time elapsing between the start of the settling period when the height of the sample is at the preselected level and the time when the detector means detects the boundary level has reached the further preselected level, in which the means for temporarily retaining the height of the sample at the preselected level during the settling period comprises a weir.

10. Sampling equipment for use in sensing the settling rate of a suspension, comprising a metering device for taking a sample of the suspension, the metering device comprising a sampling chamber for the sample, timer means for controlling control means to stop the feed of suspension to the sampling chamber, means for retaining the height of the sample at a preselected level in the sampling chamber during a settling period, and detector means for detecting when a boundary level defined by the settling solids in the sample reaches a further preselected level, the timer means determining the period of time elapsing between the start of the settling period when the height of the sample is at the preselected level and the time when the detector means detects the boundary level has reached the further preselected level, in which further detector means are provided to sense when the height of the sample in the settling chamber has reached or passed the preselected level.

11. Equipment as claimed in claim 10, in which the further detector means comprises a conductance detector having probes extending into the settling chamber.

12. Equipment as claimed in claim 10, in which the further detector means comprises a photo-electric cell device.

13. Equipment as claimed in claim 10, in which the timer means comprises sampler/timer means for controlling actuation of the metering device.

* * * * *